United States Patent
Govari et al.

(10) Patent No.: US 10,758,716 B2
(45) Date of Patent: Sep. 1, 2020

(54) PLANETARY GEAR ASSEMBLY FOR SPUTTERING MULTIPLE BALLOON CATHETER DISTAL ENDS

(71) Applicant: BIOSENSE WEBSTER (ISRAEL) LTD., Yokneam (IL)

(72) Inventors: Assaf Govari, Haifa (IL); Yehuda Algawi, Binyamina (IL); Ilya Sitnitsky, Nahariya (IL)

(73) Assignee: BIOSENSE WEBSTER (ISRAEL) LTD., Yokneam (IL)

( * ) Notice: Subject to any disclaimer, the term of this patent is extended or adjusted under 35 U.S.C. 154(b) by 462 days.

(21) Appl. No.: 15/433,528

(22) Filed: Feb. 15, 2017

(65) Prior Publication Data

US 2018/0229011 A1    Aug. 16, 2018

(51) Int. Cl.
*B23Q 3/00* (2006.01)
*A61M 25/10* (2013.01)
(Continued)

(52) U.S. Cl.
CPC ....... *A61M 25/1029* (2013.01); *A61B 5/0422* (2013.01); *A61B 5/065* (2013.01); *A61B 5/6852* (2013.01); *A61B 18/1492* (2013.01); *A61B 34/20* (2016.02); *A61L 31/00* (2013.01); *C23C 14/042* (2013.01); *C23C 14/205* (2013.01); *C23C 14/46* (2013.01); *C23C 14/505* (2013.01); *H01J 37/20* (2013.01); *H01J 37/32715* (2013.01); *H01J 37/32779* (2013.01); *A61B 2017/00053* (2013.01); *A61B 2017/00526* (2013.01); *A61B 2018/0022* (2013.01); *A61B 2018/00351* (2013.01); *A61B 2018/00577* (2013.01); *A61B 2034/2051* (2016.02); *A61M 2025/1031* (2013.01); *A61M 2207/10* (2013.01); *H01J 2237/201* (2013.01);
(Continued)

(58) Field of Classification Search
CPC ... B23Q 1/00; B23Q 1/03; B23Q 1/25; B23Q 1/70; B23Q 3/00
See application file for complete search history.

(56) References Cited

U.S. PATENT DOCUMENTS 5,391,199 A    2/1995  Ben-Haim
6,239,724 B1   5/2001  Doron et al.
(Continued)

FOREIGN PATENT DOCUMENTS

CN    103834926 A    6/2014
WO    1996005768 A   2/1996

OTHER PUBLICATIONS

Extended European Search Report for European Application No. EP18156630, dated Jul. 5, 2018, 7 pages.

*Primary Examiner* — Lee D Wilson
(74) *Attorney, Agent, or Firm* — Etan S. Chatlynne; Roberts Calderon Safran & Cole P.C.

(57) ABSTRACT

An apparatus includes an assembly and hollow templates. The assembly includes multiple hinges mounted thereon. The assembly is configured to rotate about a first axis, and each of the hinges is additionally configured to rotate about a respective second axis. The hollow templates are fitted on the respective hinges and are each configured to contain a balloon-based distal end of a medical instrument, each template having a patterned opening through which one or more electrodes are deposited on the distal end.

8 Claims, 2 Drawing Sheets

(51) Int. Cl.
    *A61B 18/14*     (2006.01)
    *A61B 34/20*     (2016.01)
    *A61B 5/06*     (2006.01)
    *A61B 5/042*     (2006.01)
    *A61B 5/00*     (2006.01)
    *C23C 14/20*     (2006.01)
    *C23C 14/46*     (2006.01)
    *C23C 14/50*     (2006.01)
    *C23C 14/04*     (2006.01)
    *H01J 37/32*     (2006.01)
    *H01J 37/20*     (2006.01)
    *A61L 31/00*     (2006.01)
    *A61B 18/00*     (2006.01)
    *A61B 17/00*     (2006.01)

(52) U.S. Cl.
    CPC ............ *H01J 2237/20214* (2013.01); *H01J 2237/20285* (2013.01); *H01J 2237/332* (2013.01)

(56) References Cited

U.S. PATENT DOCUMENTS

| | | | |
|---|---|---|---|
| 6,332,089 B1 | 12/2001 | Acker et al. | |
| 6,484,118 B1 | 11/2002 | Govari | |
| 6,618,612 B1 | 9/2003 | Acker et al. | |
| 6,690,963 B2 | 2/2004 | Ben-Haim et al. | |
| 7,448,606 B1 * | 11/2008 | Johnson | B05B 13/0285 269/16 |
| 8,460,333 B2 | 6/2013 | Boyle et al. | |
| 9,533,126 B1 | 1/2017 | Tayebi | |
| 9,976,307 B2 * | 5/2018 | Albers | E02D 27/42 |
| 2002/0065455 A1 | 5/2002 | Ben-Haim et al. | |
| 2003/0120150 A1 | 6/2003 | Govari | |
| 2004/0068178 A1 | 4/2004 | Govari | |
| 2005/0107870 A1 | 5/2005 | Wang et al. | |
| 2012/0315374 A1 | 12/2012 | Nguyen et al. | |
| 2015/0167304 A1 * | 6/2015 | Albers | E02D 27/42 52/749.1 |
| 2016/0310709 A1 | 10/2016 | Gotou et al. | |
| 2018/0229011 A1 * | 8/2018 | Govari | A61M 25/1029 |

* cited by examiner ately configured to rotate about a respective second axis. The hollow templates are fitted on the respective rods or shafts and are each configured to contain a balloon-based distal end of a medical instrument. Each template has a patterned opening through which one or more electrodes are deposited on the distal end.

In some embodiments, the apparatus includes a motor assembly, which is configured to rotate the assembly about the first axis in a first direction at a first angular velocity, and to rotate at least one of the rods or shafts about the respective second axis in a second direction at a second angular velocity. In other embodiments, the first direction differs from the second direction. In yet other embodiments, the apparatus includes a controller, which is configured to control the motor assembly.

In an embodiment, the apparatus includes a vacuum chamber, which is configured to contain the assembly in vacuum environment. In another embodiment, the apparatus includes a sputtering target made from a given material, which is configured to sputter atoms or ions of the given material in the vacuum chamber.

In some embodiments, each of the hollow templates includes an intrusion that fits a protrusion on the balloon-based distal end. In other embodiments, each of the hollow templates includes a protrusion that fits an intrusion on the balloon-based distal end.

There is additionally provided, in accordance with an embodiment of the present invention, a method for producing medical instruments. The method includes inserting into multiple hollow templates respective balloon-based distal ends of the medical instruments. The hollow templates are fitted on multiple respective rotatable rods or shafts that are mounted on a rotatable assembly. The distal ends are rotated by simultaneously rotating the assembly about a first axis, and each of the rods or shafts about a respective second axis. Electrodes are deposited, through patterned openings in the templates, on the rotated distal ends.

There is additionally provided, in accordance with an embodiment of the present invention, a method for producing a rotatable assembly. The method includes providing a rotatable assembly that is configured to rotate about a first axis. Multiple rotatable rods or shafts, which are configured to rotate about respective second axes, are mounted on the rotatable assembly. The assembly and the rods or shafts are connected to a motor assembly. Multiple hollow templates, having patterned openings, are fitted on the multiple rotatable rods or shafts.

The present invention will be more fully understood from the following detailed description of the embodiments thereof, taken together with the drawings in which:

DETAILED DESCRIPTION OF EMBODIMENTS

Overview

Balloon catheters are used in various interventional cardiology procedures, such as in treating arrhythmia, by forming lesions that block electrical conduction along a path of tissue in a patient heart. A lesion that blocks undesired intra-heart electrical signals may be formed using various techniques, such as by electrophysiology (EP) mapping of the tissue, and then applying a radio-frequency (RF) ablation to the tissue at a selected location.

One possible ablation solution is to insert to the desired ablation site an inflatable balloon assembly having an array of ablation electrodes. Conventional production techniques for depositing the electrodes on the balloon surface typically support the production of only one balloon at a time, and are therefore slow.

Embodiments of the present invention that are described hereinbelow provide improved techniques for depositing electrodes on multiple balloons at the same time using sputtering techniques at affordable cost. One example deposition process is sputtering, in which a vacuum chamber is pumped to a vacuum base pressure before sputtering, and vented to atmospheric pressure after the sputtering so as to setup the chamber for accepting the next object for sputtering.

In some embodiments, a planetary gear assembly is used for processing a batch of multiple balloon assemblies using a single process cycle that requires only one setup operation. Since the disclosed planetary gear assembly handles multiple balloon assemblies in each session in the vacuum chamber, the setup time per balloon assembly is reduced considerably.

In an embodiment, the gear assembly is configured to rotate about its longitudinal axis, while at the same time, multiple rods or shafts mounted on the gear assembly are each configured to rotate about its own respective longitudinal axis. Each rod or shaft is fitted with a respective balloon-shaped hollow template, which is configured to contain a balloon assembly on which the electrodes are to be positioned. In an embodiment, each template has a patterned opening through which one or more electrodes are deposited at high lateral resolution on the respective balloon assembly during the batch sputtering process.

The disclosed techniques enable batch processing of multiple balloon assemblies at reduced cost and cycle time, without compromising on the uniformity of the layers of the electrodes deposited using the sputtering techniques.

System Description

Figure 1:
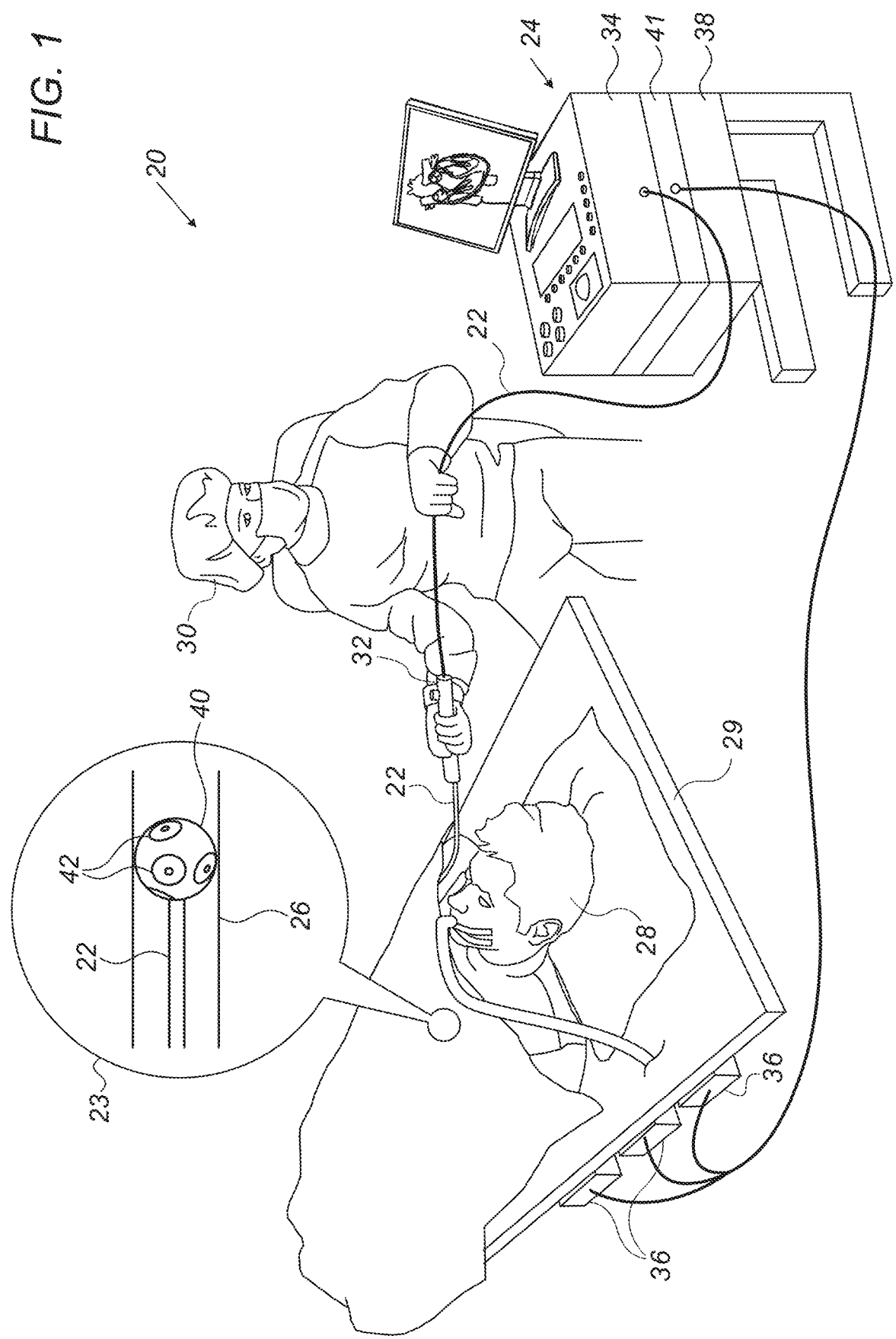
FIG. 1 is a schematic, pictorial illustration of a catheter-based tracking and ablation system, in accordance with an embodiment of the present invention.

FIG. 1 is a schematic, pictorial illustration of a catheter-based tracking and ablation system 20, in accordance with an embodiment of the present invention. System 20 comprises a catheter 22, in the present example a cardiac catheter, and a control console 24. In the embodiment described herein, catheter 22 may be used for any suitable therapeutic and/or diagnostic purposes, such as ablation of tissue in a heart (not shown).

Console 24 comprises a processor 41, typically a general-purpose computer, with suitable front end and interface circuits 38 for receiving signals via catheter 22 and for controlling the other components of system 20 described herein.

Reference is now made to an inset 23. A physician 30 inserts catheter 22 through a blood vessel 26 of the vascular system of a patient 28 lying on a table 29. Catheter 22 comprises a balloon assembly 40 fitted at its distal end. In some embodiments, assembly 40 comprises an inflatable balloon (not shown) made from polyethylene terephthalate (PET) or any other suitable flexible material. In some embodiments, balloon assembly 40 comprise electrodes 42 that may be used for multiple purposes, such as electrophysiology (EP) mapping of tissue, or for ablating tissue at a target location of the heart.

In some embodiments, ablation electrodes 42 are deposited on the external surface of balloon assembly 40 using a suitable geometrical pattern that fits the shape of the organ in question and the corresponding medical procedure (e.g., EP mapping, tissue ablation).

Several techniques may be used for applying the deposition, such as sputtering techniques, as will be described in detail in relation to FIGS. 2, 3A and 3B below.

During the insertion of catheter 22, balloon assembly 40 is contained in a sheath (not shown) in a collapsed position. In an embodiment, physician 30 navigates balloon assembly 40 in the vicinity of the target location in the heart by manipulating catheter 22 with a manipulator 32 near the proximal end of the catheter. The proximal end of catheter 22 is connected to interface circuitry in processor 41.

In an embodiment, after navigating assembly 40 to the target location, physician 30 may inflate balloon assembly 40 so as to make physical contact between electrodes 42 and tissue at the target location. In an embodiment, electrodes 42 are configured to receive electrical ablation signals, such as radio-frequency (RF), via suitable wires that run through catheter 22, and to ablate tissue at the target location in the patient heart.

In some embodiments, the position of balloon assembly 40 in the heart cavity is measured by a position sensor (not shown) of a magnetic position tracking system. In this case, console 24 comprises a driver circuit 34, which drives magnetic field generators 36 placed at known positions external to patient 28 lying on table 29, e.g., below the patient's torso. The position sensor is configured to generate position signals in response to sensed external magnetic fields from field generators 36. The position signals are indicative of the position of balloon assembly 40 in the coordinate system of the position tracking system.

This method of position sensing is implemented in various medical applications, for example, in the CARTO™ system, produced by Biosense Webster Inc. (Diamond Bar, Calif.) and is described in detail in U.S. Pat. Nos. 5,391,199, 6,690,963, 6,484,118, 6,239,724, 6,618,612 and 6,332,089, in PCT Patent Publication WO 96/05768, and in U.S. Patent Application Publications 2002/0065455 A1, 2003/0120150 A1 and 2004/0068178 A1, whose disclosures are all incorporated herein by reference.

Processor 41 typically comprises a general-purpose computer, which is programmed in software to carry out the functions described herein. The software may be downloaded to the computer in electronic form, over a network, for example, or it may, alternatively or additionally, be provided and/or stored on non-transitory tangible media, such as magnetic, optical, or electronic memory.

Figure 2:
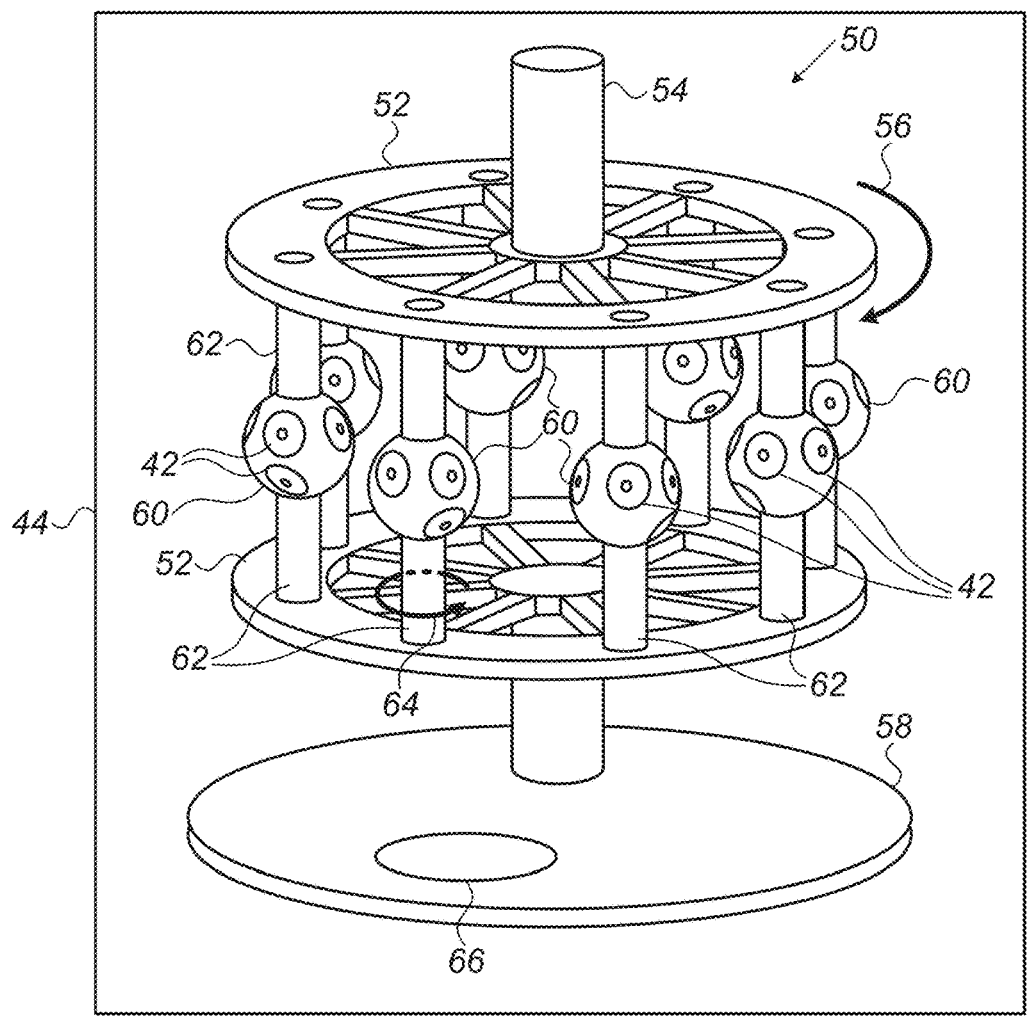
FIG. 2 is a schematic, pictorial illustration of a process chamber used for sputtering electrodes on multiple balloon assemblies, in accordance with an embodiment of the present invention.

Simultaneous Sputtering of Electrodes on Multiple Balloons Using a Planetary Gear Assembly FIG. 2 is a schematic pictorial illustration of a process chamber 44 used for sputtering electrodes 42 on multiple balloon assemblies 40, in accordance with an embodiment of the present invention. In some embodiments, chamber 44 is configured to operate at a vacuum base pressure on the order of $10^{-6}$ Torr so as to enable the sputtering of electrodes 42 on the balloon assemblies.

In some embodiments, chamber 44 comprises a planetary gear assembly 50. A sputtering target 66 is positioned on a wall 58 of chamber 44. In an embodiment, target 66 is made from gold or any other suitable material that will be deposited on balloon assembly 40, so as to serve as a conductive biocompatible material in electrodes 42.

In some embodiments, assembly 50 comprises two flat plates 52 that are mounted on a central hinge 54 substantially parallel to one another and to target 66. In an embodiment, central rod or shaft 54 is configured to rotate about its longitudinal axis clockwise (as shown by an arrow 56) or counterclockwise (not shown).

In some embodiments, assembly 50 comprises multiple rods or shafts 62 mounted between plates 52. In some embodiments, rods or shafts 62 are mounted orthogonally to plates 52 and parallel to one another.

In some embodiments, a hollow template, such as a mask assembly 60 is mounted on each rod or shaft 62. In an embodiment, each mask assembly 60 is configured to contain a respective balloon assembly 40 being fabricated, or any other balloon-based distal end of a medical instrument.

In an embodiment, mask assembly 60 has patterned openings through which, during the sputtering process, electrodes 42 are deposited on selected locations of assembly 40 that are exposed by the patterned openings. Further embodiments related to the deposition of the target material (e.g., gold) through the pattern openings are described in details in FIGS. 3A and 3B below.

In some embodiments, each rod or shaft 62 is configured to rotate about its longitudinal axis counterclockwise (as shown by an arrow 64), or clockwise (not shown), independently of other rods or shafts 62. In other words, rods or shafts 62 may rotate in an opposite direction (or alternatively, in the same direction) to the rotation of rod or shaft 54, so as to obtain uniform deposition of electrodes 42 on balloon assembly 40. In an embodiment, each mask assembly 60 is rotating together with the respective rod or shaft 62 on which the mask assembly is mounted.

In an embodiment, during the sputtering process an electron beam (not shown) impinges on target 66 (under environmental vacuum conditions as described above) so as to sputter gold atoms or ions from target 66. The sputtered gold atoms deposit via the openings in mask assemblies 60 onto the appropriate locations on balloon assemblies 40, so as to form electrodes 42.

In some embodiments, assembly 50 rotates about axis 54 continuously at a first angular velocity. In addition, each rod or shaft 62 rotates about its own longitudinal axis together with its respective mask assembly 60, at a second angular velocity. In an embodiment, the first and second angular velocities are synchronized so that mask assembly 60 completes one or more full rotations while passing next to target 66, which results in uniform deposition of gold on each of multiple assemblies 40. In another embodiment, any suitable arrangement of the first and second angular velocities may be applied so as to obtain uniform deposition of gold on each of multiple assemblies 40.

In some embodiments, after the formation of electrodes 42, each assembly 40 (whose production has been completed) may be fitted to the distal end of catheter 22 and folded to its collapsed position within the sheath, so that catheters 22 is ready to be used by physician 30.

In some embodiments, gear assembly 50 comprises a motor assembly (not shown), which comprises one or more electrical motors and a gear. Each motor is connected to the gear that translates the rotation of the motor to respective rotations of rods or shafts 54 and 62.

In an embodiment, the motor assembly comprises a single electrical motor and a gear system. The rotation of the motor is translated by the gear system so as to rotate rod or shaft 54 and all rods or shafts 62. In this embodiment, the motor assembly may be positioned externally to chamber 44, e.g., below wall 58, or alternatively, in the chamber.

In another embodiment, any suitable arrangement of motors and gears may be used.

In an embodiment, to carry out the sputtering process described above, a controller (not shown) is configured to control the motion of rods or shafts 54 and 62, e.g., by controlling the motor assembly. In some embodiments, the controller is further configured to control various process parameters, such as the vacuum level within chamber 44 and the attributes of an electron beam (not shown) impinging on target 66.

The controller typically comprises a general-purpose processor, which is programmed in software to carry out the functions described herein. The software may be downloaded to the computer in electronic form, over a network, for example, or it may, alternatively or additionally, be provided and/or stored on non-transitory tangible media, such as magnetic, optical, or electronic memory.

The configuration of gear assembly 50 shown in FIG. 2 is an example configuration that is chosen purely for the sake of conceptual clarity. In alternative embodiments, any other suitable configuration can be used. For example, plates 52 may be mounted on rod or shaft 54 at any other suitable orientation relative to one another and to target 66, and rods or shafts 62 may be mounted at any other suitable orientation with respect to plates 52. In the example of FIG. 2, rod or shaft 54 rotates clockwise and all rods or shafts 62 rotate counterclockwise. In another embodiment, the controller of assembly 50 may rotate each rod or shaft 62 at any suitable direction and angular velocity for achieving the desired level of deposition uniformity of electrodes 42.

In an alternative embodiment, instead of using an electron beam, the sputtering process may be carried out using other techniques, such as plasma-assisted sputtering. In this embodiment, an inert gas, such as argon, is ionized (e.g., using radio-frequency (RF) power) so that the ionized gas impinges on target 66 (instead of the electron beam), thereby depositing gold atoms through the pattern openings to form electrodes 42. Such processes typically use argon having a flow rate on the order of 15 standard cubic centimeter per minute (sccm) at a sputtering pressure on the order of several milliTorrs (mTorr).

Figure 3A:
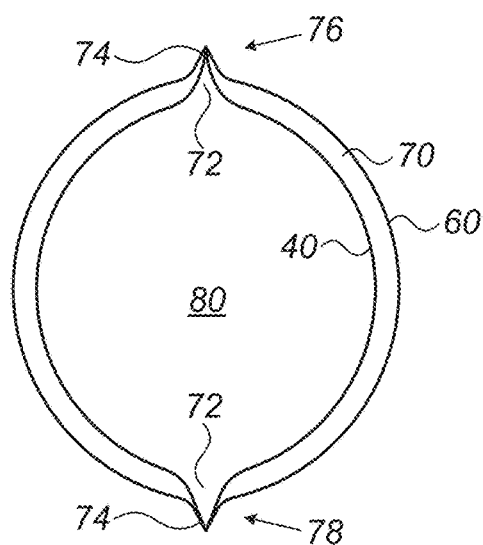
FIGS. 3A and 3B are schematic, sectional views of a balloon assembly contained in a hollow template, in accordance with embodiments of the present invention.

FIG. 3A is a schematic, sectional view of balloon assembly 40 contained within mask assembly 60, in accordance with an embodiment of the present invention. In an embodiment, the configuration depicted in FIG. 3A corresponds to a preparation phase for the sputtering process, typically by a sputtering process operator (not shown).

In some embodiments, mask assembly 60 has a substantially spherical shape and may comprise two detachable hemispheres (not shown). In an embodiment, the hemispheres are detached from one another during the insertion of balloon assembly 40 into mask assembly 60, and reattached to one another so as to contain assembly 40 therein.

In some embodiments, mask assembly 60 is made from metal, or any other suitable rigid material, which is adapted to withstand the vacuum applied in chamber 44 without its shape being deformed.

In some embodiments, balloon assembly 40 is inflated (partially or fully), typically with an inert gas 80 such as argon, before being inserted into mask assembly 60. In alternative embodiments, balloon assembly may be inflated after being inserted into mask assembly 60, or using any other suitable inflating sequence.

In an embodiment, mask assembly 60 may comprise one or more intrusions 74 that correspond with protrusions 72 of balloon assembly 40. Protrusions 72 and intrusions 74 may be used for aligning assemblies 40 and 60 to one another so as to enable accurate formation of electrodes 42 at their intended positions on assembly 40.

For example, protrusions 72 of balloon assembly 40 may serve as inflating sleeves, which are sealed at their distal ends and are substantially narrower than the maximal diameter of assembly 40 when the balloon assembly is inflated to an expanded position. In an embodiment, protrusions 72 and intrusions 74 may be located at upper pole 76 and lower pole 78 of assemblies 40 and 60, respectively. In this embodiment, protrusions 72 of assembly 40 fit into intrusions 74 of assembly 60, thereby aligning assemblies 40 and 60 to one another. In other embodiment, any suitable alternative alignment technique may be used.

In some embodiments, assembly 40 may be inflated to a degree that leaves (after being inserted into assembly 60) a spacing 70 (filled with air) between assemblies 40 and 60. In some embodiments, the operator may use spacing 70 to fine-tune the alignment between assemblies 40 and 60, before mounting assembly 60 on rod or shaft 62.

Figure 3B:
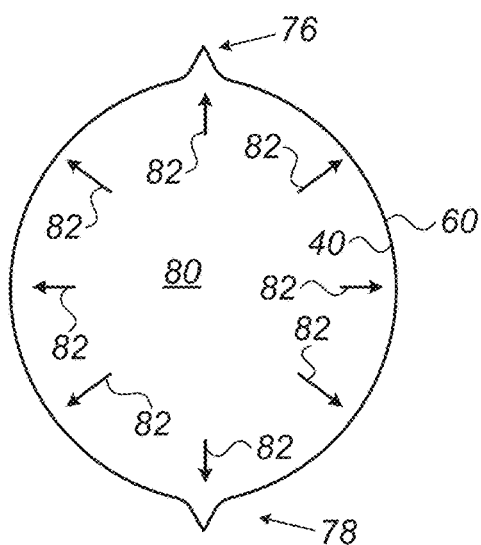

FIG. 3B is a schematic, sectional view of balloon assembly 40 contained within mask assembly 60, in accordance with an embodiment of the present invention. In an embodiment, the configuration depicted in FIG. 3B corresponds to the actual sputtering process, during which assembly 60 is held within the vacuum chamber.

In some embodiments, after aligning each pair of assemblies 40 and 60 as described in FIG. 3A above, the operator mounts each assembly 60 on its respective rod or shaft 62 and pumps the air out of chamber 44 so as to create a vacuum therein.

Due to the vacuum environment, inert gas 80 expands within assembly 40, thereby applying a radial force 82 on the inner surface of assembly 40 (which is made from flexible PET) so that assembly 40 is forced outward to become attached to mask assembly 60, and the air within spacing 70 is pumped out of chamber 44. In other words, in a presence of vacuum, the deformable external surface of balloon assembly 40 is attached to the internal surface of mask assembly 60. In an embodiment, assemblies 40 and 60 are attached to one another, so that the sputtered atoms pass through the patterned openings of assembly 60 and are deposited on assembly 40 only at the intended positions on the external surface of assembly 40, so as to form electrodes 42 thereon.

Since gas 80 is an inert gas, it does not chemically interact with any chemical element. In some embodiments, in case of a gas leakage out of assembly 40 (e.g., due to a rapture in balloon assembly 40), the presence of inert gas 80 within balloon assembly 40 prevents chemical contamination of chamber 44 and electrodes 42, or any other interference during the sputtering process.

Although the embodiments described herein mainly address sputtering on balloon catheters, the methods and systems described herein can also be used in other applications, such as sputtering electrodes on any expandable medical device.

It will be appreciated that the embodiments described above are cited by way of example, and that the present invention is not limited to what has been particularly shown and described hereinabove. Rather, the scope of the present invention includes both combinations and sub-combinations of the various features described hereinabove, as well as variations and modifications thereof which would occur to persons skilled in the art upon reading the foregoing description and which are not disclosed in the prior art. Documents incorporated by reference in the present patent application are to be considered an integral part of the application except that to the extent any terms are defined in these incorporated documents in a manner that conflicts with the definitions made explicitly or implicitly in the present specification, only the definitions in the present specification should be considered.

The invention claimed is:

1. An apparatus, comprising:
   an assembly, which comprises multiple rods mounted thereon, wherein the assembly is configured to rotate about a first axis and each of the rods is additionally configured to rotate about a respective second axis; and
   hollow templates, which are fitted on the respective rods and are each configured to contain a balloon-based distal end of a medical instrument, wherein each template has a patterned opening through which one or more electrodes are deposited on the distal end.

2. The apparatus according to claim 1, and comprising a motor assembly, which is configured to rotate the assembly about the first axis in a first direction at a first angular velocity, and to rotate at least one of the rods about the respective second axis in a second direction at a second angular velocity.

3. The apparatus according to claim 2, wherein the first direction differs from the second direction.

4. The apparatus according to claim 2, and comprising a controller, which is configured to control the motor assembly.

5. The apparatus according to claim 1, and comprising a vacuum chamber, which is configured to contain the assembly in vacuum environment.

6. The apparatus according to claim 5, and comprising a sputtering target made from a given material, which is configured to sputter atoms or ions of the given material in the vacuum chamber.

7. The apparatus according to claim 1, wherein each of the hollow templates comprises an intrusion that fits a protrusion on the balloon-based distal end.

8. The apparatus according to claim 1, wherein each of the hollow templates comprises a protrusion that fits an intrusion on the balloon-based distal end.

\* \* \* \* \*